United States Patent [19]

Gamble et al.

[11] Patent Number: 5,393,916
[45] Date of Patent: Feb. 28, 1995

[54] INHIBITION OF DIOXANE FORMATION DURING RECOVERY OF GLYCOLS FROM POLYESTER RESINS

[75] Inventors: William J. Gamble; Walter T. Gurney, both of Rochester, N.Y.

[73] Assignee: Eastman Kodak Company, Rochester, N.Y.

[21] Appl. No.: 265,302

[22] Filed: Jun. 24, 1994

[51] Int. Cl.⁶ .............................................. C07C 67/62
[52] U.S. Cl. ..................................... 560/78; 568/868; 568/871
[58] Field of Search .................... 560/78; 568/868, 871

[56] References Cited

U.S. PATENT DOCUMENTS

| | | | |
|---|---|---|---|
| 4,163,860 | 8/1979 | Delattre et al. | 560/96 |
| 5,045,122 | 9/1991 | Tindall et al. | 134/29 |
| 5,051,528 | 9/1991 | Naujokas et al. | 560/78 |
| 5,298,530 | 3/1994 | Gamble et al. | 521/48.5 |
| 5,304,673 | 4/1994 | Hermanson | 560/78 |

FOREIGN PATENT DOCUMENTS 1081681  12/1954  France.

*Primary Examiner*—José G. Dees
*Assistant Examiner*—Samuel Barts
*Attorney, Agent, or Firm*—Joshua G. Levitt

[57] ABSTRACT

There is described a process for avoiding dioxane formation during the depolymerization of polyester into glycol and ester components by passing superheated methanol through a reaction mixture containing polyester, oligomer and contaminants that are capable of forming sulfuric or halogen acids, the process comprising the step of adding sufficient base to neutralize any acid formed from the contaminants.

9 Claims, 1 Drawing Sheet

INHIBITION OF DIOXANE FORMATION DURING RECOVERY OF GLYCOLS FROM POLYESTER RESINS

FIELD OF INVENTION

This invention relates to a process for inhibiting the formation of dioxane during the recovery of glycol components from condensation-type polyester resins such as polyethylene terephthalate and polyethylene naphthalate.

BACKGROUND OF THE INVENTION

Polyester resins have found widespread use in varied applications. Polyester resins, such as polyethylene terephthalate and polyethylene naphthalate, are used in films, including photographic film and magnetic tape, in fibers, and in food containers such as beverage containers. Various methods have been disclosed for the depolymerization of such resins into their component monomers, such as ethylene glycol, terephthalic acid, naphthalic acid, or derivatives thereof, so that they could be reused.

Naujokas et al. U.S. Pat. No. 5,051,528 describes a process of recovering ethylene glycol and dimethyl terephthalate from polyethylene terephthalate scrap resins by dissolving the polyester resin in oligomers of the same monomers as present in the polyester, passing super-heated methanol through the solution and recovering ethylene glycol and dimethyl terephthalate.

Gamble et al. U.S. Pat. No. 5,298,530, issued Mar. 29, 1994 describes improvements in the process of the '528 patent in which the scrap resin is combined with reactor melt in a dissolver, before the dissolver melt is transferred to the reactor for contact with super-heated methanol. In the reactor, polymers and oligomers are futher depolymerized into the component glycol and ester monomers, which are then recovered.

The processes described in these patents have numerous advantages. These include low cost, high efficency and the ability to be used with a variety of forms of polyester of varying degrees of cleanliness and purity. Thus, suitable feedstock to the dissolver can be magnetic tape, polyester food containers, such as soda bottles, and photographic film, which may contain residual layers containing trace amounts of silver halide, magnetic iron oxide and other compounds found in photographic films, such as sulfur compounds. In addition, the processes are sufficently adaptable that they can be used with feed stock other than polymer. For example, they could be used to recover components from polyester oligomer, or to purify monomer, such as dimethylterephthalate, that has become contaminated during or after its manufacture.

However, a problem with the process is that under some conditions p-dioxane (hereinafter, dioxane) is formed. Since dioxane is a potentially harmful material, it is highly desirable to avoid is formation.

SUMMARY OF THE INVENTION

We have found that some of the scrap fed to the reactor can contain components that form compounds that can act as a catalyst for the formation of dioxane. We believe that dioxane is formed by an acid catalyzed dehydration reaction of ethylene glycol, or a higher glycol, under elevated temperature. The acid catalyst for dioxane formation can be a halogen, sulfur or nitrogen acid, for example sulfuric acid or hydrochloric acid, and can be provided by sulfur, chloride or nitrogen impurities in the polymer feedstock. Photographic film may contain some residual silver halide or sulfur sensitizers. Alternatively, a chloride catalyst could come from polyvinylidene chloride polymer that is mistaken for polyethylene terephthalate.

We have found that dioxane formation can be inhibited by providing sufficient base to neutralize the acid catalyst. The base should be present at those locations where glycols are present at elevated temperatures.

Thus, the present invention provides a process for inhibiting dioxane formation during the depolymerization of polyester into glycol and ester components by passing superheated methanol through a reaction mixture containing polyester, oligomer and contaminants that under the conditions of depolymerization are capable of forming an acid catalyst for the formation of dioxane, the process comprising the step of adding sufficient base to neutralize acid formed from the contaminants.

The present invention provides an improved process for depolymerizing polyester, especially polyester photographic film base, while avoiding the formation of undesired by-products.

DETAILED DESCRIPTION OF THE INVENTION

Figure 1:
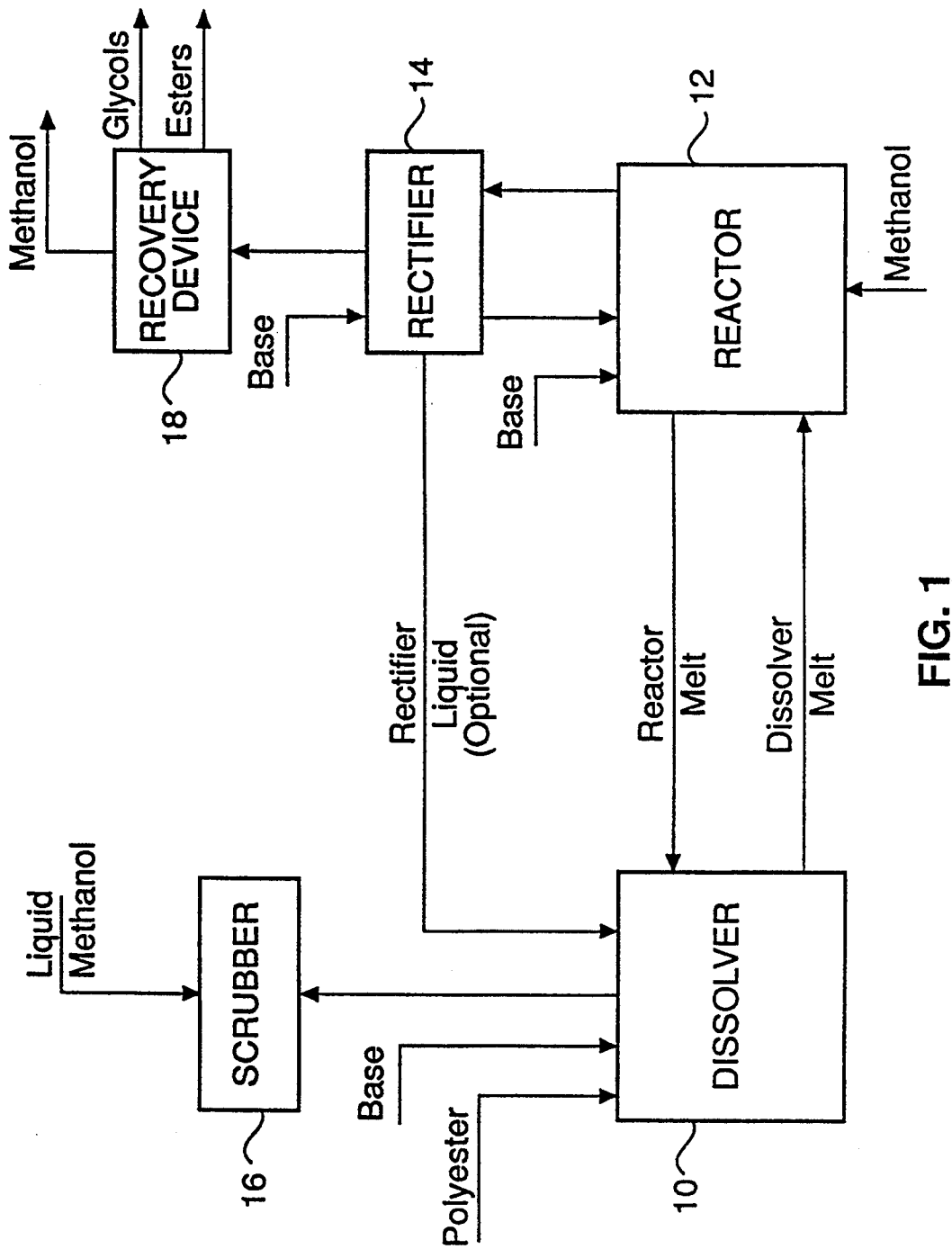
FIG. 1 is a schematic flow diagram illustrating preferred apparatus in which the process of this invention can be performed.

Tindall et al. U.S. Pat. No. 5,045,122 and French Patent 1,081,681, published Dec. 22, 1954 (which is summarized in U.S. Pat. No. 4,163,860, issued Aug. 7, 1979) describe the use of hydroxides in connection with the depolymerization of polyester. However, the processes described in these patents are different from the present process and use the hydroxide at a different point for a different purpose. Furthermore they do not recognize the problem of dioxane formation or provide any suggested solution for it.

In a preferred process of this invention the reaction is carried out using apparatus comprising:
  a dissolver for receiving polyester,
  a reactor for depolymerizing polyester into monomer components, and
  a rectifier for separating monomer components; the process comprising the steps of:
  a) adding polyester to the dissolver and combining it with melt from the reactor to reduce the chain length of the polyester,
  b) transferring reduced chain length polyester from the dissolver to the reactor,
  c) passing super-heated methanol through the reactor to depolymerize polyester into its constituent monomers,
  d) transferring depolymerization products from the reactor to the rectifier; and
  e) separating the depolymerization products in the rectifier into a vapor phase containing monomer components and a liquid phase containing higher molecular weight materials;
  wherein the base is added to one or more of the dissolver, the reactor or the rectifier.

In an especially preferred embodiment of this invention, i) the dissolver is operated at a temperature of 180° to 270° C. and a pressure of 80 to 150 kilopascals absolute (kPaa), ii) the reactor is operated at a temperature in the range of 180° to 305° C., and a pressure in the range of 101 to 800 kPaa, iii) the relative proportions, on a weight basis, of melt from the reactor and liquid from the rectifier fed to the dissolver is in the range of 0 to 1 parts liquid per part melt, and iv) the relative proportions on a weight basis of reactor melt plus rectifier liquid and polyester fed to the dissolver is in the range of 0 to 10 parts reactor melt plus rectifier liquid per part polyester, so that the viscosity of the polyester exiting the dissolver is maintained in the range of 0.001 to 0.2 Pascal seconds (Pa.s).

In a more preferred embodiment, the dissolver is operated at a temperature in the range of 215° to 260° C. and a pressure in the range of 90 to 130 kPaa, the reactor is operated at a temperature in the range of 220° to 285° C., and a pressure in the range of 200 to 620 kPaa, the relative proportions, on a weight basis, of melt from the reactor and liquid from the rectifier fed to the dissolver is in the range of 0 to 0.5 parts liquid per part melt, the relative proportions on a weight basis of reactor melt plus rectifier liquid and polyester fed to the dissolver is in the range of 0.2 to 1 parts reactor melt plus rectifier liquid per part polyester, and the viscosity of the polyester exiting the dissolver is maintained in the range of 0.002 to 0.1 Pa.s In a further preferred embodiment, the dissolver is operated at a temperature in the range of 240° to 255° C. and a pressure in the range of 95 to 105 kPaa, the reactor is operated at a temperature in the range of 250° to 280° C., and a pressure in the range of 240 to 410 kPaa, the relative proportions, on a weight basis, of melt from the reactor and liquid from the rectifier fed to the dissolver is in the range of 0 to 0.25 parts liquid per part melt, the relative proportions on a weight basis of reactor melt plus rectifier liquid and polyester fed to the dissolver is in the range of 0.2 to 0.4 parts reactor melt plus rectifier liquid per part polyester, and the viscosity of the polyester exiting the dissolver is maintained in the range of 0.01 to 0.04 Pa.s.

When operated in this way, the residence time of the polyester in the dissolver required to completely liquify the polyester is in the range of 10 to 90 minutes. Preferably it is in the range of 10 to 70 minutes and most preferably it is in the range of 30 to 65 minutes. Average residence time in the dissolver is equal to the volume of material in the dissolver divided by the rate at which material exits the dissolver.

In the following description of this invention polyethylene terephthalate will be used to illustrate the practice of the invention. It will be understood that the invention is applicable to other condensation polyesters, to oligomers and to monomers.

FIG. 1 schematically illustrates apparatus to carry out the process of the invention. It comprises a dissolver 10, a reactor 12 and a rectifier 14, connected by the pipes, pumps and valves to transfer the materials in accordance with the process of the invention. Also shown is a scrubber 16, for recovering gases from the dissolver, and a recovery device 18, for recovering monomer components and methanol vapor exiting the rectifier.

In practice polyethylene terephthalate (20) in a suitable form and size is introduced into the dissolver by any suitable means where it is liquified and reduced in chain length. The dissolver can be run at atmospheric pressure. Thus, simple solids handling devices such as rotary air locks can be employed to introduce the polyester resin. Suitable means for introducing the polyester include an air conveyor, a screw feeder, an extruder, and the like.

The dissolver is equipped with means for heating its contents to a temperature of up to about 305° C. In practice the dissolver is maintained at a temperature in the range of 240° to 260° C.

Reactor melt (22) and rectifier liquid (24) are introduced into the dissolver via suitable piping. Valves can be placed in their flow path to control the rate of introduction of these materials and their relative proportions. The reactor and rectifier are run at a higher pressure than the dissolver, thus eliminating the need for pumping means to transfer reactor melt and rectifier liquid to the dissolver, although pumping means can be employed, if desired.

Reactor melt and rectifier liquid introduced into the dissolver react with the polyester to shorten the average chain length. This initiates the depolymerization reaction and decreases the viscosity of the dissolver contents. In addition, there can be added to the dissolver an ester exchange catalyst, such as zinc acetate. Such catalysts are known in the art to facilitate the depolymerization process. The catalyst can be employed in a range of 0 to 800 parts by weight per million parts by weight of solid polyester introduced into the dissolver (ppm polyester). Preferably the catalyst is employed in the range of 30 to 300 ppm polyester, and most preferably the catalyst is employed in the range of 30 to 100 ppm polyester.

In accordance with this invention there can be added to the dissolver sufficient base (25) to neutralize acid formed from contaminants that are carried into the dissolver with the polyester scrap. Suitable bases are sodium hydroxide, potassium hydroxide, lithium hydroxide, aluminum hydroxide, sodium carbonate, potassium carbonate, and the like. Generally sufficient base is added to maintain the pH equivalent of the melt in the range of 7 to 10; preferably 7 to 8. When sodium hydroxide is used as the base it would be introduced in an amount in the range of 0.001 to 10 g per kg of polyester; preferably 0.004 to 0.01 g base per 10 kg of polyester. Equivalent amounts of different bases can be employed. The base can be introduced by any convenient means. It can be introduced as a solid with the scrap polyester, or separately, or it could be dissolved in a suitable solvent, such as ethylene glycol, and added as a liquid. Since the materials in the system have long residence times, the base can be introduced intermittently.

In a preferred embodiment, the melt in the dissolver is protected from the atmosphere by a blanket of nitrogen. This reduces degradation of the dissolver melt due to oxidation reactions.

The reactor melt and dissolver melt comprise methanol, low molecular weight polyesters, monomers, monohydric alcohol-ended oligomers, glycols, and dimethylterephthalate and methylhydroxyethyl terephthalate.

The major difference between these two melts is the average chain length of the polyester. The rectifier liquid contains the same components except for polyesters.

As indicated above, the viscosity of the dissolver melt preferably is maintained in the range of 0.002 to 0.1 Pa.s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The dissolver also can be equipped with means for removing contaminants that are introduced with the polyester. Most contaminants are removed from the melt in the dissolver before introduction of the dissolver melt to reactor. Inorganic contaminants such as metals or sand are removed by a filter. Polyolefins and other contaminants that float on top of the dissolver melt are drawn off.

The gases (26) which evolve in the dissolver contain monomers that preferably are recovered together with the monomers exiting the reactor. This can be accomplished by passing the gases to the scrubber where they are treated with and absorbed by liquid methanol (28). This material (30) is then passed to the recovery device where it is combined with material (32) exiting the rectifier for recovery of the monomers.

Melt (34) from the dissolver is transferred to the reactor by suitable piping and pumps. It would carry with it base introduced into the dissolver, so it is not necessary to provide a separate source of base (35) to the reactor. However, this can be done, if desired, or, alternatively, the base can be introduced into the reactor and carried back to the dissolver with reactor melt that transferred to the dissolver.

Super-heated methanol vapor (36) can be provided to the reactor by conventional means. A preferred means is described in U.S. Pat. No. 5,051,528 to supply the methanol to the reactor and recover the methanol for reuse. The methanol introduced into the reactor heats the reactor contents and acts as a depolymerization agent. The effectiveness of the super-heated methanol for heating the reactor contents and for stripping gases depends on its volumetric flow rate; the depolymerization rate in the reactor therefore is a function of the methanol flow rate to the reactor. Methanol is introduced into the reactor at a rate in the range of 2 to 6 parts by weight methanol per part polyester.

There is transferred from the reactor to the rectifier a vapor stream (38) comprising methanol, dimethylterephthalate, glycols including ethylene glycol, diethylene glycol, and triethylene glycol, dimethylisophthalate, cyclohexanedimethanol, and methylhydroxyethyl terephthalate. The rectifier separates methylhydroxyethyl terephthalate from the vapor stream exiting the reactor and returns it to the dissolver in the form of a liquid (40) together with dimethyl terephthalate, and methanol. Excess liquid (42) from the rectifier drains back into the reactor.

Since the base in the reactor is not sufficiently volatile to pass to the rectifier, additional base (43) can be introduced into the rectifier, preferably at the top, to react with and neutralize any acid that is carried over from the reactor.

The remainder of the vapor stream (44) is transferred from the rectifier to recovery apparatus, where methanol (46) can be recovered for further use, and the glycol components (48) separated from the terephthalate components (50).

While the process of this invention has been described in connection with the preferred apparatus shown in the FIGURE, it will be appreciated that base could be introduced at other locations in the process where there is the potential for acid catalysts to form and react with glycols at elevated temperatures above about 100° C.

EXAMPLES

The following examples illustrate the effectiveness of base in inhibiting the formation of dioxane during parts of a process for the recovery of monomer components from polyester.

Example 1. Dissolver Simulation

Tests were run to determine the effect of acid contaminants on p-dioxane formation in a polyester recovery system. The reactions that occur in the dissolver (10) shown in FIG. 1 were simulated by combining, in an autoclave, materials that could be found in the dissolver in amounts, in grams, shown in Table 1, below. The materials are identified as follows: PET, polyethylene scrap; DEG, diethylene glycol; TEG, triethylene glycol; HCl, 37 wt % solution of hydrochloric acid; $H_2SO_4$, 95 wt % solution of sulfuric acid; NaOH, 97 wt % pellets of sodium hydroxide; and ADD, additional components. Each combination of materials was heated at reflux in the autoclave for 2 hours, after which the composition of the reaction product was determined by gas chromatography and mass spectroscopy. The relative proportions, by weight, of the components of each reaction product is shown in Table 1, below. It will be observed that in the presence of an acid, dioxane is formed, but when the acid is neutralized with base, dioxane formation is substantially inhibited.

TABLE 1

| | Material Combined (g) | | | | Reaction Products (wt %) | | |
|---|---|---|---|---|---|---|---|
| Run # | PET | DEG | TEG | ADD | Water | Dioxane | Oligomer |
| 1 | 255 | 160 | 85 | 5HCl | 2.1 | 1.7 | 96.2 |
| 2 | 255 | 160 | 85 | 5$H_2SO_4$ | 5.3 | 20.7 | 74.0 |
| 3 | 255 | 160 | 85 | 5 $H_2SO_4$ + 10NaOH | 1.4 | 1.1 | 97.5 |

Example 2. Reactor Simulation

Example 1 was repeated except that, in order to simulate the reactions that could occur in the reactor (12) shown in FIG. 1, in addition to the materials combined in that example there were added methanol (MeOH) and zinc acetate (ZnAc) a depolymerization catalyst. The amounts of material, in grams, combined in the autoclave is shown in Table 1, below, as is the proportions of the reaction products, by weight. It will be observed that: absent the presence of an acid a negligible amount of dioxane is formed; when acid is present there is dioxane formation; but when base is added to neutralize the acid dioxane formation is substantially inhibited.

TABLE 2

| Run # | Materials Combined (g) | | | | | | Reaction Products (wt %) | | |
|---|---|---|---|---|---|---|---|---|---|
| | MeOH | PET | DEG | TEG | ZnAC | ADD | Water | Dioxane | Oligomer |
| 4 | 316 | 77 | 48 | 26 | 0.5 | — | 0.4 | 0.2 | 99.5 |
| 5 | 316 | 77 | 48 | 26 | 0.5 | 5 HCl | 1.9 | 1.4 | 96.7 |
| 6 | 316 | 77 | 48 | 26 | 0.5 | 5 HCl + 10 NaOH | 1.1 | 0.2 | 98.8 |

The invention has been described by reference to preferred embodiments, but it will be understood changes can be made to the apparatus and process steps specifically described herein within the spirit and scope of the invention.

What is claimed is:

1. A process for avoiding dioxane formation during the depolymerization of polyester into glycol and ester components by passing superheated methanol through a reaction mixture containing polyester, oligomer and contaminants that under depolymerization conditions are capable of forming acid catalysts for the formation of dioxane, the process comprising the step of adding sufficient base to neutralize acid formed from the contaminants.

2. A process of claim 1, wherein the base is added in an amount sufficient to maintain the pH equivalent of the reaction mixture in the range of 7 to 10.

3. A process of claim 1, wherein the base is added in an amount sufficient to maintain the pH equivalent of the reaction mixture in the range of 7 to 8.

4. A process of claim 1, wherein the base is selected from sodium hydroxide, potassium hydroxide, sodium carbonate and potassium carbonate.

5. A process of claim 1, wherein the base is sodium hydroxide or sodium carbonate and is added in an amount of from 0.001 to 10 g per kg of polyester.

6. A process of claim 1, wherein the contaminant forms sulfuric acid or a halogen acid.

7. A process of claim 1, wherein the polyester resin is polyethylene terephthalate.

8. A process of claim 1 wherein the process is carried out using apparatus comprising:
   a dissolver for receiving polyester,
   a reactor for depolymerizing polyester into monomer components, and
   a rectifier for separating monomer components; the process comprising the steps of:
   a) adding polyester to the dissolver and combining it with melt from the reactor to reduce the chain length of the polyester,
   b) transferring reduced chain length polyester from the dissolver to the reactor,
   c) passing super-heated methanol through the reactor to depolymerize polyester into its constituent monomers,
   d) transferring depolymerization products from the reactor to the rectifier; and
   e) separating the depolymerization products in the rectifier into a vapor phase containing monomer components and a liquid phase containing higher molecular weight materials;
   wherein the base is added to the apparatus at a location where it can react with the acid catalyst.

9. A process of claim 8, where the base is added to one or more of the dissolver, the reactor or the rectifier.

* * * * *